(12) United States Patent
Ales, III et al.

(10) Patent No.: US 7,760,101 B2
(45) Date of Patent: Jul. 20, 2010

(54) METHOD OF REDUCING SENSOR CORROSION IN ABSORBENT ARTICLES

(75) Inventors: Thomas Michael Ales, III, Neenah, WI (US); Shawn Jeffery Sullivan, Neenah, WI (US); Paul E. Jansen, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 256 days.

(21) Appl. No.: 12/214,603

(22) Filed: Jun. 20, 2008

(65) Prior Publication Data
US 2009/0315728 A1 Dec. 24, 2009

(51) Int. Cl.
*G08B 23/00* (2006.01)
(52) U.S. Cl. .................................. 340/573.5
(58) Field of Classification Search ............. 340/573.5, 340/604, 603, 592, 657, 605; 73/73; 604/361
See application file for complete search history.

(56) References Cited

U.S. PATENT DOCUMENTS

| | | | |
|---|---|---|---|
| 4,100,324 A | 7/1978 | Anderson et al. | |
| 4,704,116 A | 11/1987 | Enloe | |
| 4,800,370 A * | 1/1989 | Vetecnik | 340/573.5 |
| 4,940,464 A | 7/1990 | Van Gompel et al. | |
| 5,114,781 A | 5/1992 | Morman | |
| 5,116,662 A | 5/1992 | Morman | |
| 5,284,703 A | 2/1994 | Everhart et al. | |
| 5,350,624 A | 9/1994 | Georger et al. | |
| 5,486,166 A | 1/1996 | Bishop et al. | |
| 5,490,846 A | 2/1996 | Ellis et al. | |
| 5,645,542 A | 7/1997 | Anjur et al. | |
| 5,760,694 A * | 6/1998 | Nissim et al. | 340/604 |
| 5,766,389 A | 6/1998 | Brandon et al. | |
| 5,820,973 A | 10/1998 | Dodge, II et al. | |
| 5,838,240 A * | 11/1998 | Johnson | 340/604 |
| 5,883,028 A | 3/1999 | Morman et al. | |
| 5,903,222 A * | 5/1999 | Kawarizadeh et al. | 340/604 |
| 5,964,743 A | 10/1999 | Abuto et al. | |
| 6,097,297 A * | 8/2000 | Fard | 340/604 |
| 6,231,557 B1 | 5/2001 | Krautkramer et al. | |
| 6,362,389 B1 | 3/2002 | McDowall et al. | |
| 6,552,245 B1 | 4/2003 | Roessler et al. | |
| 6,645,190 B1 | 11/2003 | Olson et al. | |
| 6,916,968 B2 * | 7/2005 | Shapira et al. | 340/604 |
| 6,969,378 B1 | 11/2005 | Vukos et al. | |
| 7,355,090 B2 | 4/2008 | Ales, III et al. | |
| 7,498,478 B2 | 3/2009 | Long et al. | |

(Continued)

FOREIGN PATENT DOCUMENTS

WO WO 00/37009 A2 6/2000
WO WO 03/051254 A2 6/2003

*Primary Examiner*—Phung Nguyen
(74) *Attorney, Agent, or Firm*—David J Arteman

(57) ABSTRACT

Methods of reducing sensor corrosion include providing a monitor adapted to electrically connect with a wetness sensor integrated with an absorbent article. The wetness sensor has a first conductor and a second conductor and the monitor includes programming instructions that, when the monitor is attached and activated, repetitively execute a sequence of steps that includes applying voltage to the first conductor; measuring the potential across the conductors; and discontinuing the voltage to the first conductor. The instructions may also repetitively execute a sequence of steps that includes alternatively applying voltage to the first and second conductors and/or grounding the first conductor and/or second conductors after discontinuing voltage.

20 Claims, 11 Drawing Sheets

U.S. PATENT DOCUMENTS

| | | |
|---|---|---|
| 2002/0135489 A1* | 9/2002 | Chen et al. ............ 340/604 |
| 2004/0147888 A1 | 7/2004 | Huang et al. |
| 2007/0049881 A1 | 3/2007 | Ales et al. |
| 2007/0142796 A1 | 6/2007 | Mosbacher et al. |
| 2007/0142797 A1 | 6/2007 | Long et al. |
| 2007/0142799 A1 | 6/2007 | Ales et al. |
| 2007/0252710 A1 | 11/2007 | Long et al. |
| 2007/0252711 A1 | 11/2007 | Long et al. |

* cited by examiner

METHOD OF REDUCING SENSOR CORROSION IN ABSORBENT ARTICLES

BACKGROUND OF THE INVENTION

The present invention relates generally to a monitoring system adapted to detect the presence of an insult in an absorbent article while it is being worn by a wearer. More particularly, the present invention relates to wetness monitors and wetness monitoring methods that reduce the amount and/or rate of corrosion of the conductors located within the absorbent articles.

Disposable absorbent articles find widespread use as personal care products such as diapers, children's toilet training pants and other infant and child care products, adult incontinence garments and other adult care products, sanitary napkins and other feminine care products, and the like, as well as surgical bandages and sponges and medical garments. These articles absorb and contain body waste and are intended to be discarded after a limited period of use; i.e., the articles are not intended to be laundered or otherwise restored for reuse. Conventional disposable absorbent articles include an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass through for absorption by the absorbent body.

Disposable absorbent training pants, in particular, are useful in toilet training children. Typically, these disposable undergarments are similar to washable, cloth underwear in the manner in which they are put on and worn, yet provide an absorbent function similar to diapers to maintain skin health. Training pants provide a child undergoing toilet training with an undergarment that eases the transition from diapers to washable, cloth underwear as they become more confident in their ability to use the toilet independently.

Monitoring of a toilet-training child by a caregiver can be helpful in that when urination occurs it can be discussed by the child and caregiver to enhance and improve the learning experience. Therefore, it is beneficial to provide the caregiver with immediate notification and/or verification that urination has occurred so that it may be discussed with the child while the event is still fresh in the child's mind.

Likewise, caregivers tending to the hygienic needs of care recipients can benefit by monitoring the occurrences of urination in the care recipients so that the absorbent articles may be changed when necessary, but repeated inspection is not required. Therefore, it is beneficial to provide the caregiver with immediate notification that urination has occurred so that appropriate action may be taken.

One way of monitoring urination is by using a system that detects a change in an electrical property of the undergarment wherein the electrical property is a function of the wetness of the undergarment. For example, the electrical property may be resistance, conductance, impedance, capacitance or any other parameter which varies as the wetness of the undergarment varies. For example, a pair of spaced apart parallel conductors may be situated within or proximate the absorbent material of the undergarment. These conductors may be in electrical contact with the absorbent material of the undergarment and may be connected to a monitor to complete a wetness circuit including a power source, such as a battery. For example, the circuit may include a voltage divider for detecting resistance between the conductors.

The output of the circuit may be an analog output voltage that corresponds to a resistance value. When the undergarment is dry, the resistance between the conductors is expected to be extremely high and relatively infinite, appearing as an open circuit. When the undergarment is wet, more particularly when the absorbent material of the undergarment between the conductors becomes wet, the resistance of the undergarment at that area is expected to drop to a relatively lower value because urine acts as a conductor.

Accordingly, in a conventional system the resistance between the conductors is monitored and compared to a predetermined and fixed threshold resistance value. If a resistance value is less than the threshold resistance value, then the wetness circuit sends a signal to an indicator, which notifies the caregiver and/or the wearer that the wearer has urinated.

As noted above, these articles are intended to be discarded after a limited period of use. As such, the conductors are desirably thin foil strips or the like. For example, the conductors may be vapor deposited films because they can be economically produced. However, vapor deposited foils are susceptible to corrosion by electrochemical reaction which can result in electrical performance loss. Once urine insults the product, aluminum ions from the conductors are removed and put in mobile phase across the potential of the open electronic circuit. Within a short amount of time, the foils lose electrical continuity along the length of the product making wetness detection difficult or inaccurate.

Several parameters influence this electrochemical reaction. First, aluminum is a very reactive metal within electrochemical cells and the ions of the urine are a perfect electrochemical solution to encourage the active transfer of the metal ions from the conductor to the mobile phase. Second, even a small potential difference applied across the conductors can have significant effect on the duration of the conductors' continuity. Finally, in near-body sensor systems, like those discussed herein, DC power is preferable because it is simple, it satisfies the power needs, and it is safe. However, DC power has been found to greatly accelerate the corrosion of the conductors.

Thus, despite their usefulness, conventional devices may be prone to corrosion by electrochemical reaction. Accordingly, there is a need for wetness monitoring systems that provide wetness notification and a method of reducing sensor corrosion.

SUMMARY OF THE INVENTION

In response to the discussed need, one aspect of the present invention provides a method of reducing sensor corrosion in an absorbent article. The method includes providing a monitor adapted to electrically connect with a wetness sensor integrated with an absorbent article. The wetness sensor has a first conductor and a second conductor. The monitor includes programming instructions that, when attached to the sensor in the absorbent article and activated, executes a sequence of steps. The sequence of steps includes applying voltage to the first conductor of the wetness sensor, measuring the potential across the conductors, and discontinuing the voltage to the first conductor. The sequence of steps is repetitively executed at least one time per second and the voltage is applied to the first conductor for 10% or less of the time and the voltage is discontinued to the first conductor 90% or more of the time.

In various embodiments, the instructions may further include repetitively executing the sequence of steps at least three times per second. In various embodiments, the voltage may be applied to the first conductor for 5% or less of the time and the voltage may be discontinued to the first conductor 95% or more of the time.

In some embodiments, the instructions may further include repetitively executing the sequence of steps at a first frequency for a first time period and repetitively executing the sequence of steps at a second frequency for a second time period wherein the first frequency and the second frequency are different.

In some embodiments, the instructions may further include the step of grounding the first conductor after discontinuing the voltage to the first conductor. In some embodiments, the instructions may further include the steps of applying voltage to the second conductor after discontinuing the voltage to the first conductor, measuring the potential across the conductors, and discontinuing the voltage to the second conductor. In some embodiments, the instructions may further include the steps of grounding the first conductor after discontinuing the voltage to the first conductor and grounding the second conductor after discontinuing the voltage to the second conductor.

In another aspect, the present invention provides a method of reducing sensor corrosion in an absorbent article. The method includes providing a monitor adapted to electrically connect with a wetness sensor integrated with an absorbent article. The wetness sensor has a first conductor and a second conductor. The monitor includes programming instructions that, when attached to the sensor in the absorbent article and activated, repetitively executes a sequence of steps. The sequence of steps includes applying voltage to the first conductor, measuring the potential across the conductors, discontinuing the voltage to the first conductor, applying voltage to the second conductor, measuring the potential across the conductors, and discontinuing the voltage to the second conductor.

In various embodiments, method may include repetitively executing the sequence of steps at least one time per second. In some embodiments, the method may include repetitively executing the sequence of steps at least three times per second. In various embodiments, the instructions may further include repetitively executing the sequence of steps at a first frequency for a first time period and repetitively executing the sequence of steps at a second frequency for a second time period wherein the first frequency and the second frequency are different.

In some embodiments, the voltage may be applied to the first conductor for 10% or less of the time and the voltage may be discontinued to the first conductor 90% or more of the time. In some embodiments, the voltage may be applied to the second conductor for 10% or less of the time and the voltage may be discontinued to the second conductor 90% or more of the time.

In some embodiments, the instructions may further include the step of grounding the first conductor after discontinuing the voltage to the first conductor. In some embodiments, the instructions may further include the steps of grounding the first conductor after discontinuing the voltage to the first conductor and grounding the second conductor after discontinuing the voltage to the second conductor.

In another aspect, the present invention provides a method of reducing sensor corrosion in an absorbent article. The method includes providing a monitor adapted to electrically connect with a wetness sensor included in an absorbent article. The wetness sensor having a first conductor and a second conductor. The monitor includes programming instructions that, when attached to the absorbent article and activated, repetitively executes a sequence of steps. The sequence of steps includes applying voltage to the first conductor, measuring the potential across the conductors, discontinuing the voltage to the first conductor, grounding the first conductor, applying voltage to the second conductor, measuring the potential across the conductors, discontinuing the voltage to the second conductor, and grounding the second conductor.

In various embodiments, the instructions may further include the step of repetitively executing the sequence of steps at least one time per second. In some embodiments, the instructions may further include repetitively executing the sequence of steps at least three times per second.

In some embodiments, the instructions may further include repetitively executing the sequence of steps at a first frequency for a first time period and repetitively executing the sequence of steps at a second frequency for a second time period wherein the first frequency and the second frequency are different.

In some embodiments, the voltage may be applied to the first conductor for 10% or less of the time and the voltage may be discontinued to the first conductor 90% or more of the time and the voltage may be applied to the second conductor for 10% or less of the time and the voltage may be discontinued to the second conductor 90% or more of the time.

BRIEF DESCRIPTION OF THE DRAWINGS

Corresponding reference characters indicate corresponding parts throughout the drawings.

DETAILED DESCRIPTION OF THE DRAWINGS

The monitors and absorbent articles of the present invention are adapted to form all or part of a monitoring system for detecting the presence of an insult (e.g., urine, feces, menstrual fluid, blood, and the like). In general, one or more sensors are used to detect the insult. The system monitors an electrical property of the sensor (e.g., resistance, conductivity, and the like) and based on the changes in the electrical property, determines whether the absorbent article has been insulted. After detecting the presence of the insult, a caregiver and/or a wearer of the absorbent article is signaled as to the presence of the insult. The signal may be, for example, an auditory signal, such as a song; and/or a tactile signal, such as temperature change, pressure, and/or vibration; and/or a visual signal, such as a blinking light, a visual message, or the like. It will be understood that other signals are within the scope of the present disclosure. It is also understood that the monitoring system may include a device for sending a wireless signal to a remote auditory, visual, tactile or other sensory alarm.

Absorbent Articles

Figure 1:
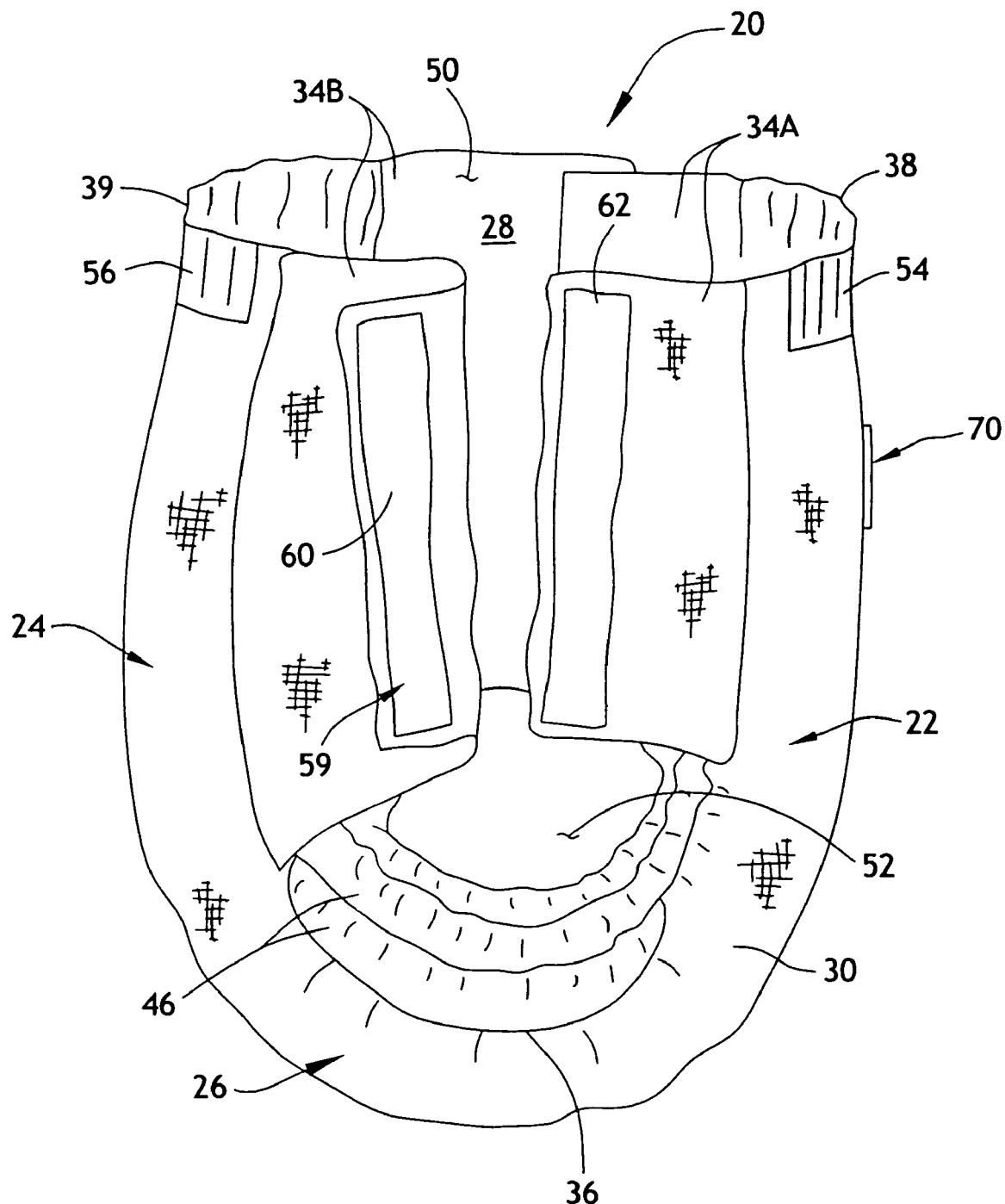
FIG. 1 is a side perspective view of an exemplary article adapted to function as part of a wetness monitoring system.

Referring now to the drawings and in particular to FIG. 1, an exemplary absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like, without departing from the scope of the present invention.

By way of illustration only, various materials and methods for constructing training pants are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 4:
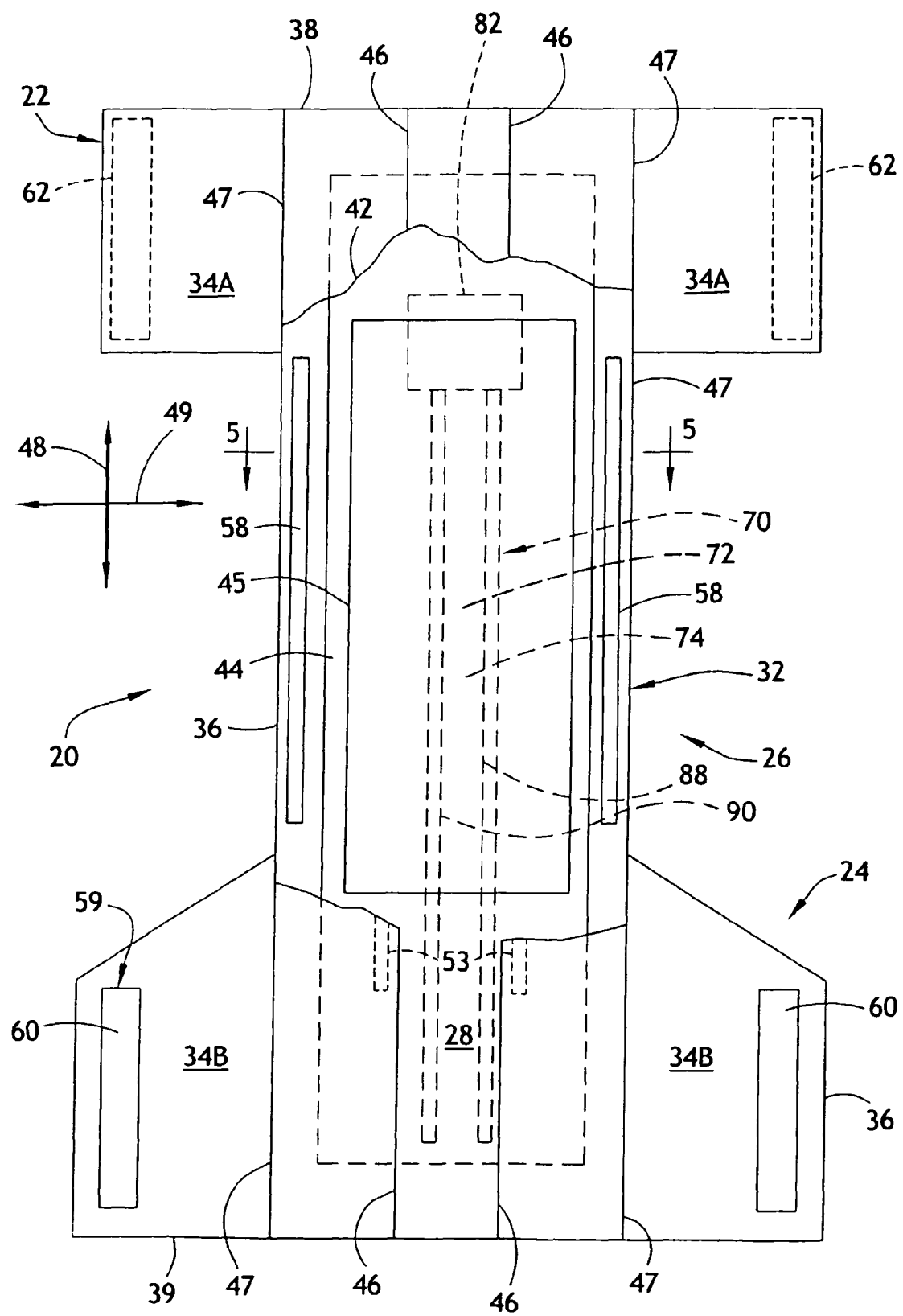
FIG. 4 is a top plan view of the training pants of FIG. 1 with the pants in an unfastened, unfolded and laid flat condition, with portions cut away to show underlying features.

The training pants 20, of FIG. 1, are illustrated in a partially fastened condition. The pants 20 define a longitudinal direction 48 and a lateral direction 49 thereof perpendicular to the longitudinal direction as shown in FIG. 4. FIG. 4 is a top plan view of the training pants of FIG. 1 with the pants in an unfastened, unfolded and laid flat condition, with portions cut away to show underlying features. The pants 20 further define a pair of longitudinal end regions, otherwise referred to herein as a front waist region, generally indicated at 22, and a back waist region, generally indicated at 24, and a center region, otherwise referred to herein as a crotch region, generally indicated at 26, extending longitudinally between and interconnecting the front and back waist regions 22, 24. The front and back waist regions 22, 24 include those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 that faces toward the wearer when the pants are being worn, and an outer surface 30 opposite the inner surface. With additional reference to FIG. 4, the pair of training pants 20 has a pair of laterally opposite side edges 36 and a pair of longitudinally opposite waist edges (broadly, longitudinal ends), respectively designated front waist edge 38 and back waist edge 39.

In various embodiments, including those illustrated in FIGS. 1-4, the training pants 20 may include a generally rectangular central absorbent assembly, generally indicated at 32, and side panels 34A, 34B formed separately from and secured to the central absorbent assembly. The side panels 34A, 34B may be permanently bonded along seams to the central absorbent assembly 32 in the respective front and back waist regions 22 and 24 of the pants 20. More particularly, the front side panels 34A may be permanently bonded to and extend transversely outward beyond side margins 47 of the absorbent assembly 32 at the front waist region 22, and the back side panels 34B may be permanently bonded to and extend transversely outward beyond the side margins of the absorbent assembly at the back waist region 24. The side panels 34A and 34B may be bonded to the absorbent assembly 32 using attachment means known to those skilled in the art such as adhesive, thermal or ultrasonic bonding, or the like, or combinations thereof.

The front and back side panels 34A and 34B, upon wearing of the pants 20, thus include the portions of the training pants 20 which are positioned on the hips of the wearer. The front and back side panels 34A and 34B may be permanently bonded together to form the three-dimensional configuration of the pants 20 (see e.g., FIGS. 2 and 3), or be releasably connected with one another such as by a fastening system 59 (see e.g., FIGS. 1 and 4). As is known in the art, the side panels 34A, 34B may include elastic material or stretchable but inelastic materials.

The absorbent assembly 32 is illustrated in FIG. 4 as having a rectangular shape. However, it is contemplated that the absorbent assembly 32 may have other shapes (e.g., hourglass, T-shaped, I-shaped, and the like) without departing from the scope of this invention. It is also understood that the side panels 34A, 34B may instead be formed integrally with the absorbent assembly 32 without departing from the scope of this invention.

Figure 5:
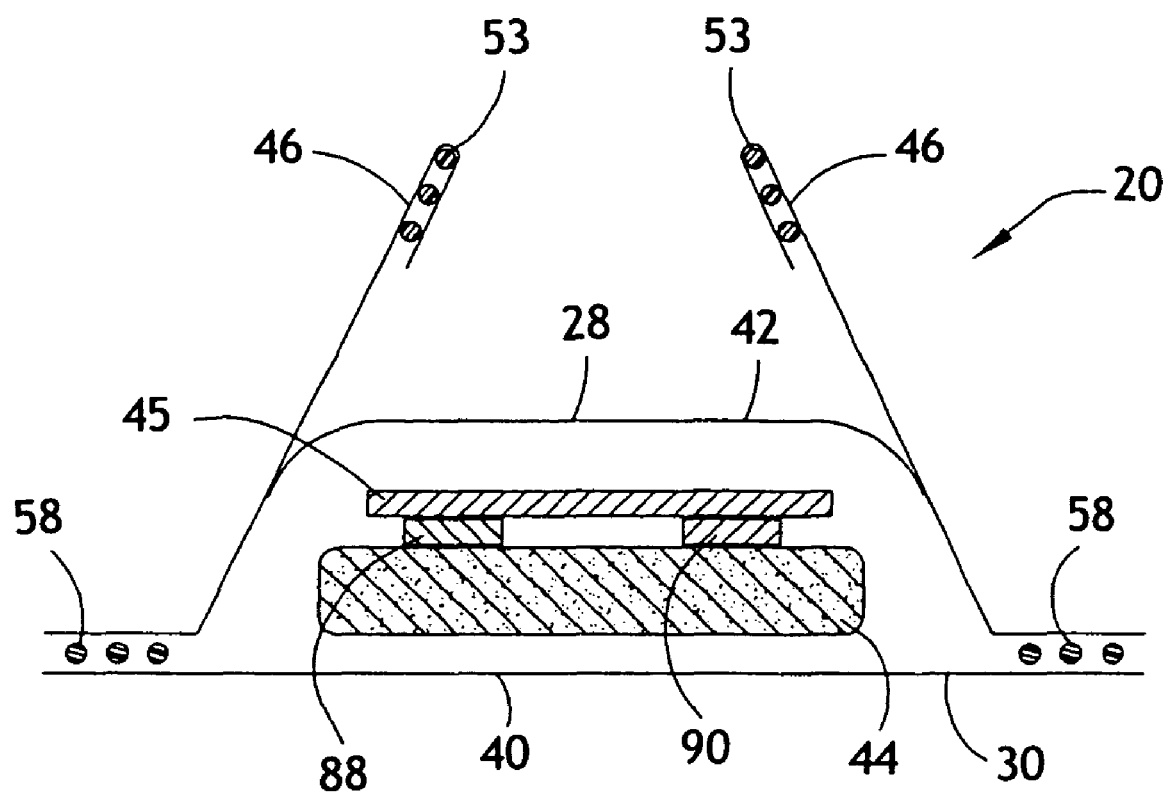
FIG. 5 is cross-sectional view of the pants of FIG. 4 taken along the line 5-5.

As illustrated in FIGS. 4 and 5, the absorbent assembly 32 may include an outer cover 40 and a bodyside liner 42 attached to the outer cover 40 in a superposed (opposed) relation therewith by adhesives, ultrasonic bonds, thermal bonds, pressure bonds, or other conventional techniques, or combinations thereof. The liner 42 may be suitably joined to the outer cover 40 along at least a portion of the longitudinal ends of the pants 20. In addition, the liner 42 may be suitably joined to the outer cover 40. The liner 42 may be suitably adapted, i.e., positioned relative to the other components of the pants 20, for contiguous relationship with the wearer's skin during wear of the pants. The absorbent assembly 32 may also include an absorbent structure 44 disposed between the outer cover 40 and the bodyside liner 42 for absorbing liquid body exudates exuded by the wearer and may include a surge management layer 45 disposed between the absorbent structure and the bodyside liner. A pair of containment flaps 46 may be secured to the bodyside liner 42 for inhibiting the lateral flow of body exudates.

With the training pants 20 in the fastened position as partially illustrated in FIG. 1, the front and back waist regions are connected together by the fastening system 59 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

As illustrated in FIG. 4, a flap elastic member 53 may be operatively joined with each containment flap 46 in any suitable manner as is well known in the art. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may include a front waist elastic member 54 (FIG. 1), a rear waist elastic member 56, and leg elastic members 58 (FIGS. 2-4), as are known to those skilled in the art. The flap elastic members 53, the waist elastic members 54 and 56, and the leg elastic members 58 can be formed of any suitable elastic material known to those skilled in the art.

The fastening system 59 of the illustrated embodiment includes laterally opposite first fastening components 60 adapted for refastenable engagement to corresponding laterally opposite second fastening components 62. In one embodiment, a front or outer surface of each of the fastening components 60, 62 includes a plurality of engaging elements. The engaging elements of the first fastening components 60 are adapted to repeatedly engage and disengage corresponding engaging elements of the second fastening components 62 to releasably secure the pants 20 in its three-dimensional configuration. The fastening components 60, 62 can include any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably includes a material that is substantially liquid impermeable. The outer cover 40 may include a single layer of liquid impermeable material, or more suitably include a multi-layered laminate structure in which at least one of the layers is liquid impermeable. While it is not a necessity for the outer layer to be liquid permeable, it is suitable that it provides a relatively cloth-like texture to the wearer. Alternatively, the outer cover 40 may include a woven or nonwoven fibrous web layer that has been totally or partially constructed or treated to impart the desired levels of liquid impermeability to selected regions that are adjacent or proximate the absorbent structure. The outer cover 40 may also be stretchable, and in some embodiments it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. The bodyside liner 42 may also be stretchable, and in some embodiments it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al. both of which are incorporated by reference herein, for additional information regarding bodyside liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents, or the like, as well as combinations thereof.

The materials may be formed into an absorbent web structure by employing various conventional methods and techniques known in the art. For example, the absorbent structure 44 may be formed by a dry-forming technique, an air-forming technique, a wet-forming technique, a foam-forming technique, or the like, as well as combinations thereof. Methods and apparatus for carrying out such techniques are well known in the art. The absorbent structure 44 may alternatively include a coform material such as the material disclosed in U.S. Pat. Nos. 4,100,324 to Anderson, et al.; U.S. Pat. No. 5,284,703 to Everhart, et al.; and U.S. Pat. No. 5,350,624 to Georger, et al.; which are incorporated herein by reference. Optionally, a substantially liquid permeable wrapsheet (not shown) may surround the absorbent structure 44 to help maintain the integrity of the absorbent structure 44.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one embodiment, the absorbent structure 44 may be stretchable so as not to inhibit the stretchability of other components to which the absorbent structure may be adhered, such as the outer cover 40 and bodyside liner 42. For example, the absorbent structure may include materials disclosed in U.S. Pat. Nos. 5,964,743, 5,645,542, 6,231,557, 6,362,389, and international patent application WO 03/051254, the disclosure of each of which is incorporated by reference herein.

The surge management layer 45 may be attached to various components of the article 20 such as the absorbent structure 44 and/or the bodyside liner 42 by methods known in the art, such as by adhesive, ultrasonic or thermal bonding. The surge management layer 45 helps to decelerate and diffuse surges or gushes of liquid that may be rapidly introduced into the absorbent structure 44 of the article 20. Desirably, the surge management layer 45 can rapidly accept and temporarily hold the liquid prior to releasing the liquid into the storage or retention portions of the absorbent structure 44. Examples of suitable surge management layers 45 are described in U.S. Pat. Nos. 5,486,166; and 5,490,846. Other suitable surge management materials are described in U.S. Pat. No. 5,820,973. The entire disclosures of these patents are incorporated by reference herein.

Monitoring Systems

In general, the monitoring systems of the present invention include a wetness circuit. The wetness circuit generally includes one or more conductors, a voltage source and a measuring device. The measuring device measures an electrical property of the wetness circuit, e.g., resistance, conductance, voltage, etc., and sends a signal containing information regarding the electrical property to a microprocessor. The microprocessor analyzes the signal to determine if an insult has occurred. If an insult has occurred, an indicator is activated to signal a caregiver and/or wearer of the absorbent article of the presence of the insult.

Figure 2:
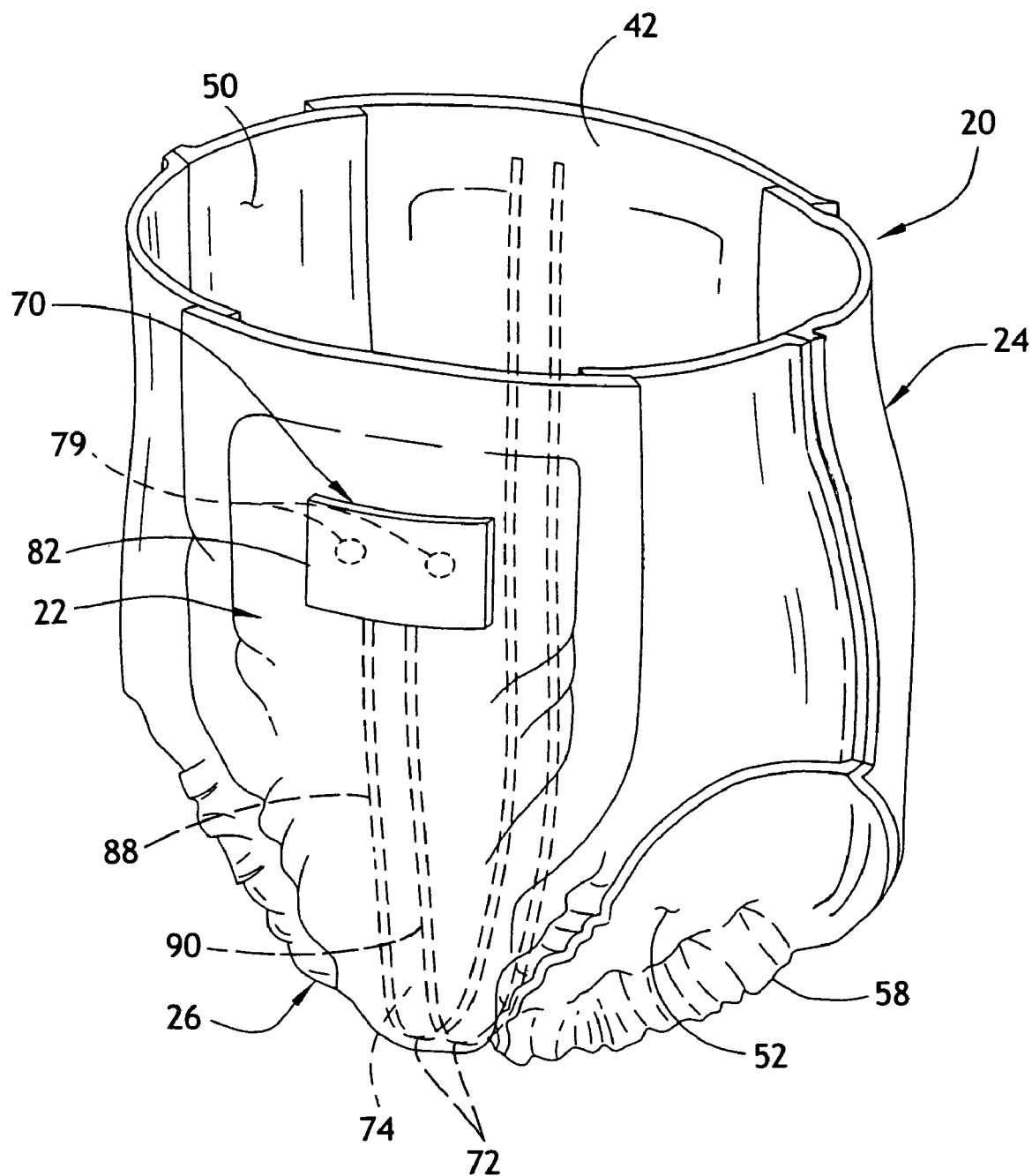
FIG. 2 is a perspective view of another exemplary article adapted to function as part of a wetness monitoring system.
Figure 3:
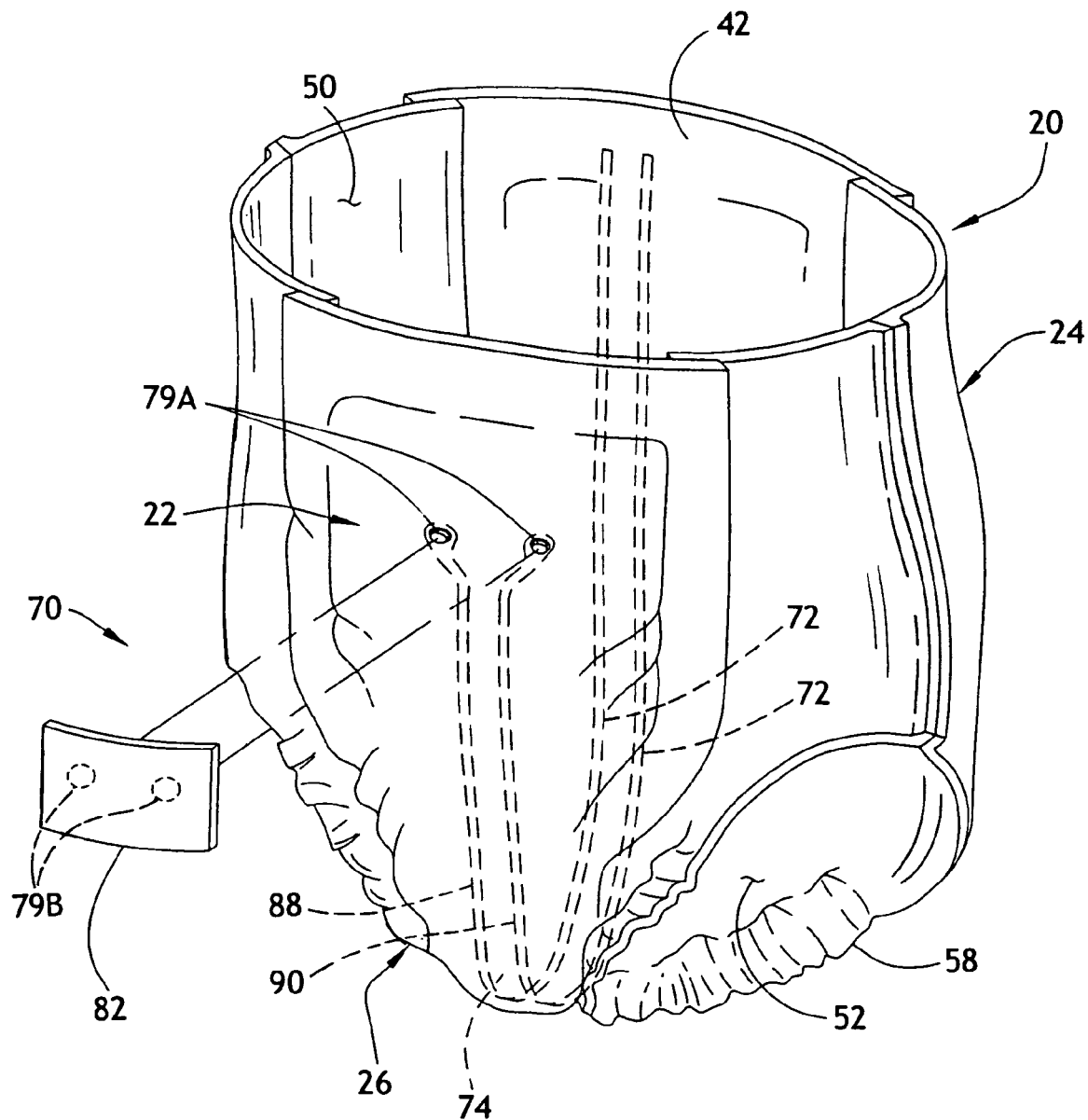
FIG. 3 is a perspective view of the pants of FIG. 2 showing the housing of a monitoring system removed from the article.

In the illustrated embodiments, the training pants 20 of the present invention form a portion of a wetness monitoring system for detecting the presence of urine (broadly, an insult) within the pants 20. As illustrated in FIGS. 2-4, an exemplary wetness monitoring system is generally indicated by reference numeral 70. The monitoring system 70 includes a sensor 72 for detecting the electrical property (e.g., resistance R) of the article. The sensor 72 may include a pair of spaced apart and generally parallel first conductor 88 and second conductor 90. The conductors 88 and 90 may be disposed at any suitable position within the pants 20. The conductors 88 and 90 may define a monitoring area 74 which may be disposed between the conductors.

The conductors 88, 90 may be constructed of any material that is generally electrically conductive. For example, the conductors may be constructed of metal strips (e.g., aluminum strips), metal films, coated films, conductive polymers, conductive inks, conductive threads, or the like, or combinations thereof. Other conductors are within the scope of this invention. As illustrated, the conductors 88, 90 may extend longitudinally from the front waist region 22, through the crotch region 26, to the back waist region 24 of the pants 20. As shown best in FIG. 5, the conductors 88, 90 may be disposed within the absorbent assembly 32 between the absorbent structure 44 and the surge management layer 45, although the conductors may be disposed at other locations without departing from the scope of this invention.

Figure 6:
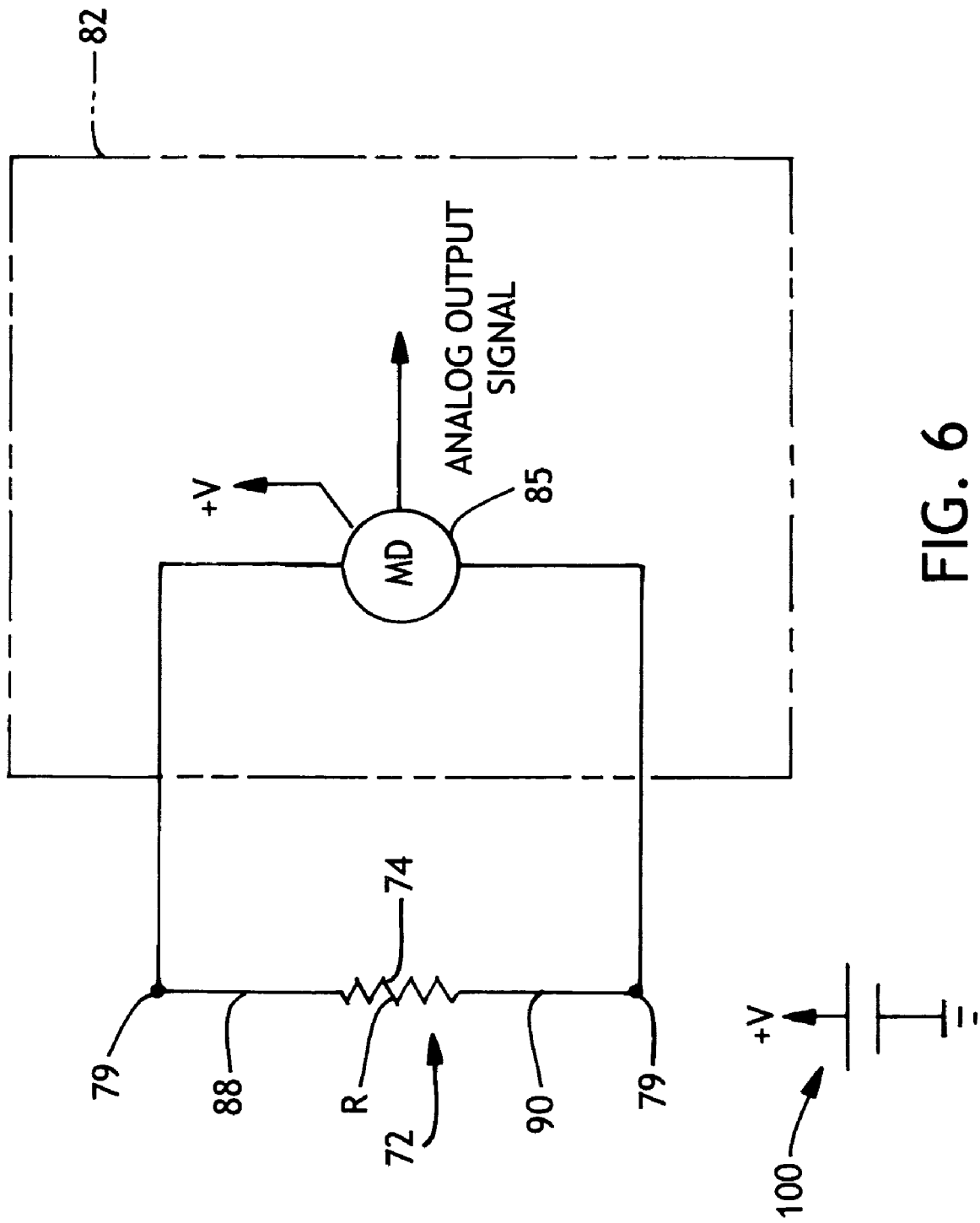
FIG. 6 is a schematic illustration of one embodiment of a wetness monitoring system of the present invention.

When activated, voltage from a voltage source 100 (illustrated schematically in FIG. 6) is applied to the first conductor 88 or the second conductor 90 of the sensor 72. The voltage source 100 may be a direct voltage source such as a battery (as illustrated), or an alternating voltage source. The conductors 88 and 90 may be electrically connected to the voltage source by any suitable contacts. For example, the contacts of the voltage source may be electrically connected with the conductors 88, 90 through one or more orifices located in one or more materials of the absorbent article. Alternatively or additionally, the contacts of the voltage source may pierce through one or more materials of the absorbent article to electrically connect with the conductors 88, 90.

In the illustrated embodiment of FIGS. 2 and 3, the conductors 88, 90 are electrically connected to the voltage source by way of electrically conductive snap fasteners 79. However, any suitable means of electrically connecting the conductors to the voltage source are within the scope of this disclosure. Suitable means of electrically connecting the conductors, include, for example, a clamp connector, conductive hook and loop fasteners, conductive adhesives (e.g., conductive tape), electrically conductive contacts, electrically conductive pins, and the like, and combinations thereof. Suitable methods of electrically connecting the conductors to the voltage source are disclosed in commonly assigned U.S. patent application Ser. No. 11/303,283 to Long et al., filed on Dec. 15, 2005, entitled "Garments With Easy-To-Use Signaling Device" and U.S. patent application Ser. No. 11/303,222 to Mosbacher et al., filed on Dec. 15, 2005, entitled "Garments With Easy-To-Use Signaling Devices", the entirety of each are incorporated herein by reference where not contradictory.

As used herein, the term "electrically connected" or "electric connection" or derivatives thereof describes two or more objects positioned and/or configured such that current may flow to or from one object to the second object. In other words, these terms refer to a first contact, conductor, circuitry, or the like, being positioned and/or configured such that current may flow to or from a second contact, conductor, circuitry, or the like. In some embodiments, an electrical connection may also be a physical connection, such as through snaps, hooks, or the like. In some embodiments, an electrical connection may include two or more contacts, conductors, circuitry, that are touching, and therefore allow current to flow, but are not physically connected together.

As will be apparent from the discussion herein, the components of the monitoring system (e.g., measuring device, voltage source, microprocessor, analog-to-digital converter, indicator, transmitter, and/or receiver, etc.) may be housed together or separately, and may be attached to the absorbent article or may be present at a remote location. For example, in one embodiment, the measuring device, microprocessor, voltage source, analog-to-digital converter, and/or transmitter are housed together and are attached to the absorbent article, while the receiver and/or indicator are housed together at a remote location. As used herein, "remote location" means the components are not attached to the absorbent article. For example, in one embodiment, the receiver and/or indicator may be housed in a transportable unit that may be kept with the caregiver. Examples of such a unit may include an alarm such as a bed side alarm, alarm clock, beeper, or pager, a lamp, a wall clock, and the like.

As illustrated in FIGS. 2 and 3, each corresponding end of each conductor 88, 90 of the sensor 72 is electrically and physically connected to a first snap fastener member 79A located in the front waist region 22 of the pants 20. In some embodiments, the first snap fastener member may be located in the back waist region 24, or other locations on the pants 20. A housing 82 that houses a voltage source 100 has corresponding second snap fastener elements 79B for engaging the first snap fasteners 79A and securing the housing 82 to the pants 20. In addition to the voltage source 100, the housing 82 of the present embodiment may also house the remaining components of the wetness monitoring system 70 that will be described hereinafter, although it is contemplated that the housing 82 may include only some or none of the remaining components. In the illustrated embodiment, the housing 82 is releasably secured to the pants 20 by way of the snap fasteners 79, although it is understood that the housing 82 may be releasably secured to the pants 20 by other fasteners, such as for example, receptacles, sockets, adhesives, cohesives, magnets, hooks and loops, clips, clamps, snaps, pockets, straps, and the like, and combinations thereof. Alternatively, the housing 82 may be permanently secured to the pants by any suitable means without departing from the scope of this invention.

A measuring device 85 (FIG. 6), electrically connected with the sensor 72, measures an electrical property of the monitoring area 74 of the pants 20. In one embodiment, the resistance, R, of the monitoring area 74 of the pants 20 is measured. Because the conductors 88, 90 are spaced apart, current from the voltage source 100 must pass through the monitoring area 74 to complete the circuit. As illustrated schematically in FIG. 6, the monitoring area 74 acts essentially as a resistor, as representatively indicated by reference character R. When the monitoring area 74 is dry (e.g., before the presence of an insult), the resistance of the monitoring area is relatively high, for example, some resistance above 200 k$\Omega$ (kilo ohms). When the monitoring area 74 is wetted, for example by an insult, its resistance drops, for example, to some resistance less than 200 k$\Omega$ because of the electrically conductive nature of urine.

In various embodiments, the conductors 88 and 90 may be connected by any suitable resistor or resistors located in the monitoring area 74, such as, for example, a chemiresistor to complete the circuit. Suitable chemiresistors are taught in U.S. patent application Ser. No. 11/314,438 to Dong et al., filed Dec. 21, 2005, entitled "Personal Care Products With Microchemical Sensors For Odor Detection", the entirety of which is incorporated herein by reference where not contradictory.

In another embodiment, the conductance of the monitoring area 74 of the pants 20 may be measured. As stated above, urine is electrically conductive and the article 20 generally is not electrically conductive. Therefore, when the monitoring area 74 of the pants 20 is wetted, its conductance is greater than when it is dry. Other electrical properties of the pants 20, including, for example, impedance and voltage drop, may be measured without departing from the scope of this invention.

The measuring device 85 produces an analog output signal (FIG. 6) indicative of the electrical property of the monitoring area 74 of the pants 20. For example, the measuring device 85 can measure a voltage drop across the monitoring area 74, and produce an analog output signal corresponding to the voltage drop. The output voltage signal can be used to determine other electrical properties, such as resistance or current, by performing suitable calculations known in the art or using a reference table. For example, as is well known in the art, the voltage drop is indicative of the resistance of the pants when the current is constant. Thus, the resistance of the pants 20 may be determined using the analog output signal of the measuring device 85. In various embodiments, the measuring device may be integral with a microprocessor or may provide an output signal to a microprocessor.

In various embodiments, any suitable method may be used to determine the presence (or lack thereof) of an insult in the absorbent article. For example, suitable methods are disclosed in U.S. patent application Ser. No. 11/215,937 to Long et al., filed on Aug. 31, 2005, entitled "Method Of Detecting The Presence Of An Insult In An Absorbent Article And Device For Detecting The Same"; U.S. patent application Ser. No. 11/216,977 to Collins et al., filed on Aug. 31, 2005, entitled "Method Of Detecting The Presence Of Insults In An Absorbent Article"; and U.S. patent application Ser. No. 11/215,968 to Collins et al. filed on Aug. 31, 2005, entitled "Method Of Detecting The Presence Of An Insult In An Absorbent Article", the entirety of each are incorporated herein by reference where not contradictory.

In various embodiments, the microprocessors may be programmed to activate one or more indicators at various times, for various durations, via various means as will be evident to one skilled in the art. For example, in any suitable embodiment, the microprocessor may be programmed to provide a notification to the wearer and/or caregiver when the wetness monitoring system first becomes operational. In some embodiments, the microprocessor may be adapted to notify the wearer and/or caregiver that the wetness monitoring system is operational at any suitable interval by activating one or more indicators. In some embodiments, the microprocessor may be programmed to provide notification to the wearer and/or caregiver when the wetness monitoring system becomes non-operational by activating one or more indicators. For example, the monitor may beep when continuity is detected, beep periodically while continuity is detected and beep when continuity is broken. For example, suitable operational notification systems are disclosed in U.S. Patent Publication No. 20070252710 to Long et al., entitled "Wetness Monitoring Systems With Status Notification System" the entirety of which is incorporated herein by reference where not contradictory.

In various embodiments, the voltage source may be part of a power management system. The power management systems may take various forms and generally include one or more power circuits. For example, suitable power management systems are disclosed in U.S. Patent Publication No. 20070252711 to Long et al., entitled "Wetness Monitoring Systems With Power Management," the entirety of which is incorporated herein by reference where not contradictory.

The present invention is further directed towards methods of reducing sensor corrosion. It has been found that once urine, or other body exudate, insults the absorbent article, metal ions (e.g., aluminum ions) from the conductors are removed and put in the mobile phase across the monitoring area 74 (i.e., across the open circuit). Within a short amount of time, the foils may corrode, become discontinuous, and no longer allow for measurement of the electrical property being monitored (e.g., potential, resistance, etc.). Thus, the ability to determine the wetness of the absorbent article or change in the relative wetness may be compromised.

Programming Sequences

While not wishing to be bound by theory, it is believed that by utilizing various switching schemes, ionization of the conductor particles may be reduced. For example, in one embodiment, a method of reducing sensor corrosion in an absorbent article includes providing a monitor adapted to electrically connect with a wetness sensor integrated with an absorbent article wherein the wetness sensor has a first conductor and a second conductor as discussed above. The monitor includes programming instructions that repetitively execute a sequence of steps when activated. In various embodiments, any suitable method of activation is contemplated. For example, activation may occur when the monitor is attached to the absorbent article. In other examples, activation may occur when the monitor becomes electrically connected with the conductors. In some embodiments, activation may occur when a switch is closed.

In various embodiments, the sequence of steps may be executed by any suitable circuit including any suitable microcontroller. For example, an "H-Bridge" circuit, as illustrated generally at 102 in FIG. 7, may be used with any suitable micro-controller 104. Suitable micro-controllers 104 include, for example, the PIC16F876A available from Microchip Technology Inc. having offices in Chandler, Ariz., USA.

Figure 7:
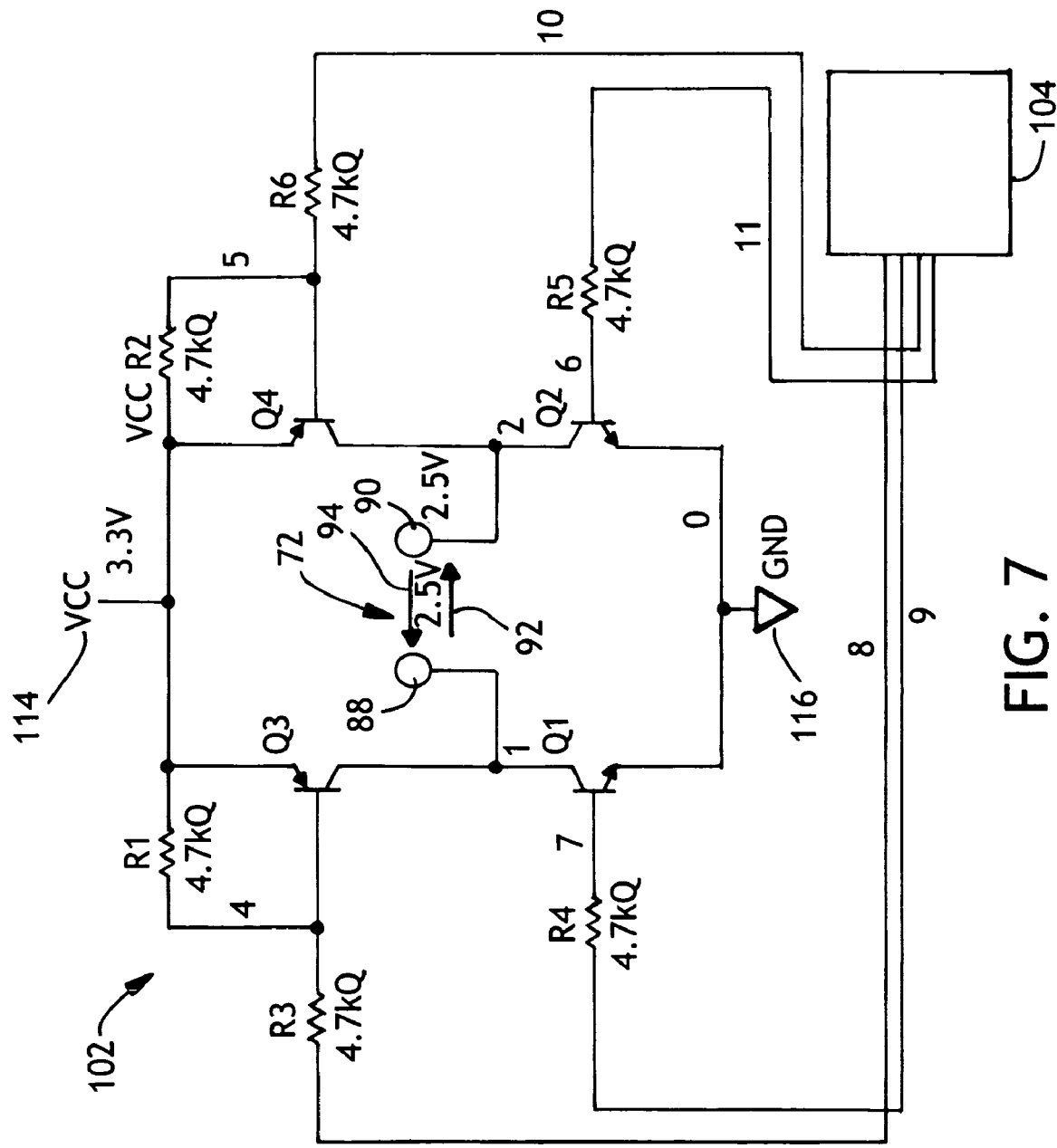
FIG. 7 is a schematic illustration of an exemplary sensing circuit.

Referring to FIG. 7, the circuit 102 may be designed to easily and quickly connect either a voltage source node (VCC) 114 or a circuit reference point, also referred to as the ground point (GND) 116 to the first conductor 88 and/or the second conductor 90. Specifically, separate outputs of the micro-controller 104 may be used to connect or disconnect transistors Q1, Q2, Q3, and/or Q4. As used herein, the phrase "connect," with reference to transistors, means the transistors are conducting current. As used herein, the phrase "disconnect," with reference to transistors, means the transistors are not conducting current. The transistors may be "connected" by forcing them into a conducting state and may be "disconnected" by forcing them into a non-conducting state.

By way of example, a first conductor 88 or a second conductor 90 may be connected to the voltage source 114 by forcing the input to the PNP-type transistors Q3 or Q4 low through the 4.7 kΩ resistors R3 or R6, respectively. Likewise, to disconnect the first conductor 88 or the second conductor 90 from the voltage source 114, the input to the PNP-type transistors Q3 or Q4 may be driven high. In some embodiments, a 47 kΩ resistor R1 or R2 from base to emitter on the PNP-type transistors Q3 and Q4 insures the transistors remain disconnected if the input to the base goes "high impedance" (no signal but still some impedance to the ground 116).

Further, by way of example, a first conductor 88 or a second conductor 90 may be connected to the ground (GND) 116 by driving the base of the NPN-type transistors Q1 or Q2 high through the R4 and R5 resistors, respectively. Likewise, the base of the NPN-type transistors Q1 or Q2 may be driven low through the R4 and R5 resistors, respectively, to disconnect the NPN transistors Q1 or Q2 from ground 116.

Figure 8:
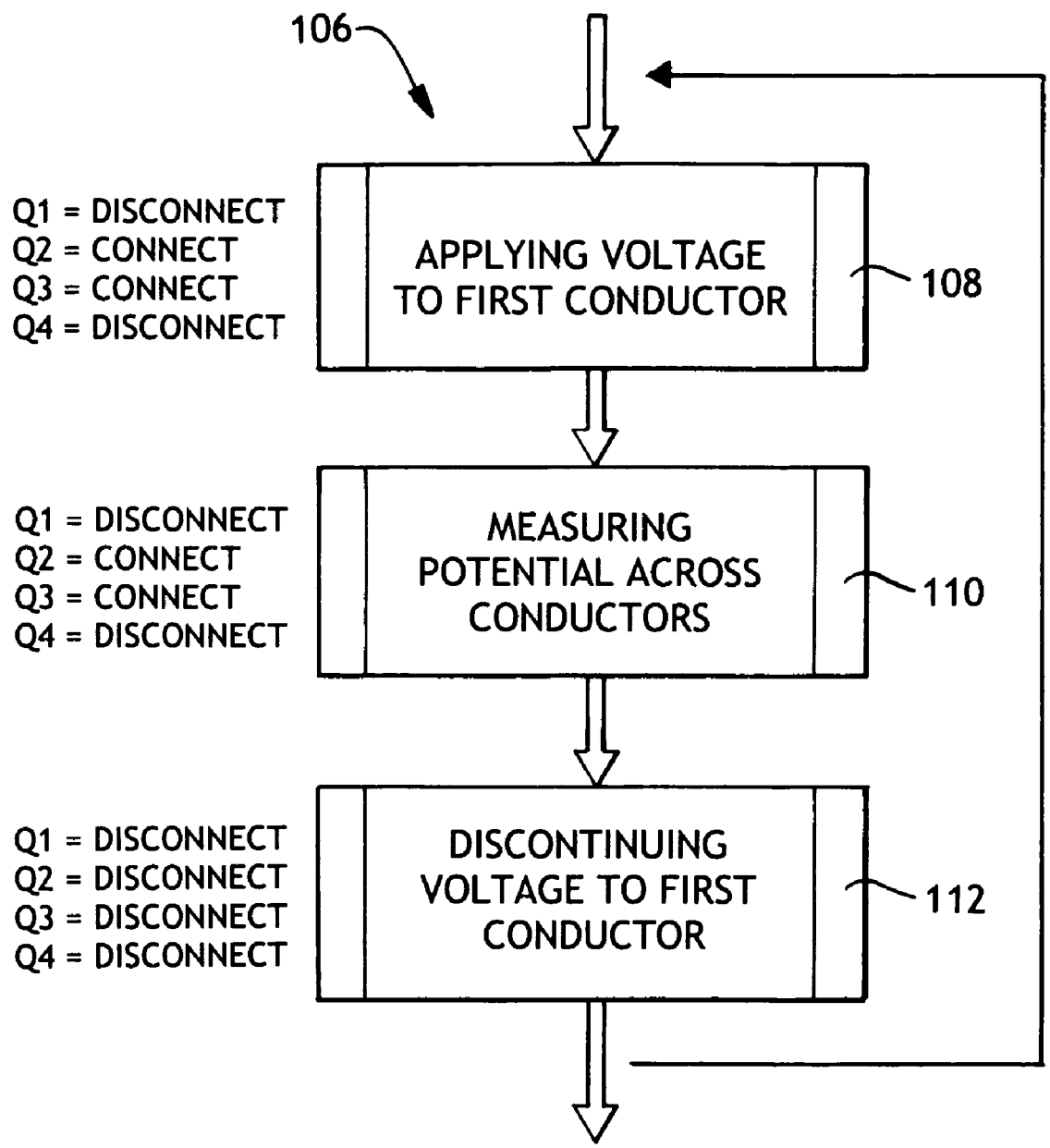
FIG. 8 is a flow diagram illustrating a sequence of programming steps of one embodiment.

In one embodiment, a microprocessor can repetitively execute a sequence of steps to selectively pulse current flow. For example, one sequence of steps directed by a microprocessor (i.e., the programming instructions) is illustrated in FIG. 8 generally at 106 and includes a step 108 of applying voltage to a first conductor 88 of a wetness sensor 72. As used herein, the term "applying voltage" means creating an electrical path wherein current from a voltage source is allowed to flow to a destination such as a conductor. Step 108 may be accomplished by connecting the transistors Q3 and Q2 while transistors Q1 and Q4 are disconnected such that the current flows from the voltage source 114 through Q3 to conductor 88 through sensor 72 (i.e., the space between the conductors) in a first direction 92 to conductor 90 and then through Q2 to ground 116.

The next step 110 in the sequence 106 includes measuring the potential across the conductors 88 and 90. Measuring the potential across the conductors is the same as measuring the voltage drop across the monitoring area between the conductors. It should be noted that voltage is a differential quantity, which appears between two points having electric potentials. Thus, when measuring the potential across the conductors, the opposite conductor (i.e., the conductor that does not have voltage applied thereto) is grounded. To measure the voltage of a single point, a reference point must be selected to measure against. This common reference point is called the ground 116 and is considered to have zero voltage. In the present invention, this signal ground 116 is not necessarily connected to the earth and may be considered a floating ground. Thus, as used herein, the terms "ground", "grounded", and "grounding" refer to a point in an electrical circuit from which other voltages are measured. The ground 116 provides a common return path for electric current.

During the step 110 of measuring the potential across the conductors, the circuit 102 remains the same as in step 108. That is, as illustrated in FIG. 7, transistors Q3 and Q2 are connected and transistors Q1 and Q4 are disconnected.

After the step 110 of measuring the potential across the conductors, the sequence 106 includes the step 112 of discontinuing the voltage to the first conductor 88. For example, referring to FIG. 7, the transistor Q3 is disconnected. Likewise, transistors Q1, Q2, and Q4 are also disconnected.

As used herein, the term "discontinuing the voltage" means stopping current from a voltage source from flowing to a destination, such as a conductor. Since the microcontroller is not directing the sampling of the conductor continuously, the conductor excitation voltage need only be applied slightly before the sampling step. Likewise, as soon as the sample has been completed, the excitation voltage may be removed and thus, the duty cycle of excitation voltage will be less than if continuously excited. Therefore, the life of the conductors is expected to be extended. In other words, the current flow is cycling between a flowing condition and a stopped condition (i.e., pulsing).

Voltage may be applied to the first conductor 88 for any suitable percentage of time. For example, in various embodiments, the voltage may be applied to the first conductor 88 for 10% or less, 5% or less, or 1% or less of the time. In other words, the first conductor 88 may have voltage applied 10% or less of the time and may have no voltage applied 90% or more of the time.

Figure 9:
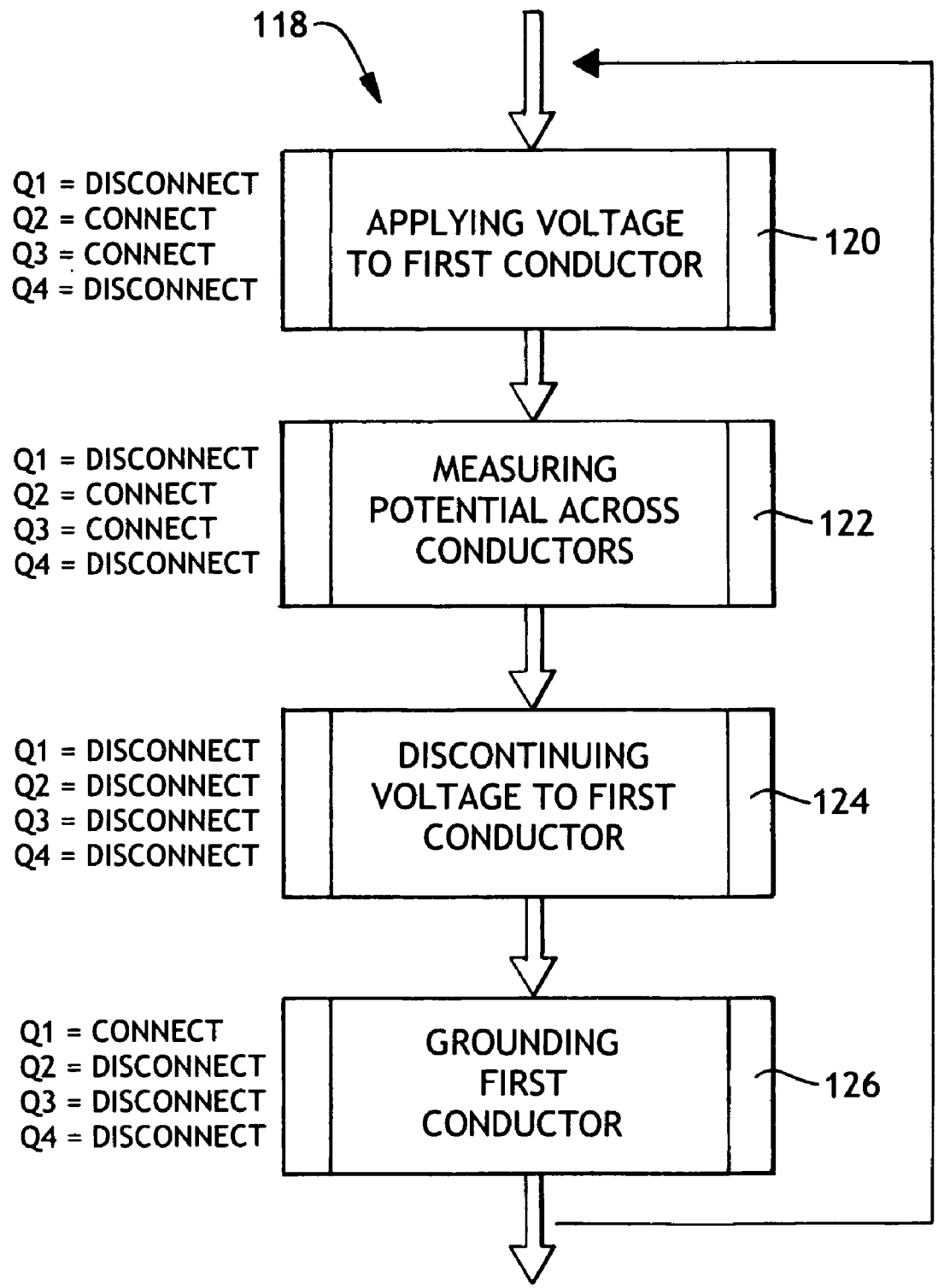
FIG. 9 is a flow diagram illustrating a sequence of programming steps of one embodiment.

In some embodiments, a sequence of steps may include the step of grounding the conductor after discontinuing the voltage to the conductor. For example, referring now to FIG. 9, a second sequence of steps is illustrated generally at 118. The second sequence of steps 118 includes a first step 120 of applying voltage to the first conductor 88. The second step 122 includes measuring the potential across the conductors 88 and 90. The third step 124 includes discontinuing the voltage to the first conductor 88. Steps one 120, two 122, and three 124 are similar to the steps 108, 110, and 112 of the first sequence 106. Specifically, in various embodiments, steps 120 and 122 may be accomplished by connecting transistors Q2 and Q3 and disconnecting transistors Q1 and Q4 as illustrated in the exemplary circuit 102 of FIG. 7. In various embodiments, step 124 may be accomplished by disconnecting transistor Q3.

The second sequence of steps 118 includes the additional step 126 of grounding the first conductor 88 after discontinuing the voltage to the first conductor 88. The additional step of grounding may be accomplished by controlling a circuit 102 as illustrated in FIG. 7. Specifically, step 126 of the second sequence 118 may be accomplished by connecting transistor Q1 while maintaining transistors Q2, Q3, and Q4 disconnected. As such, conductor 88 is disconnected from the voltage source 114 and is connected to the ground 116. By grounding the first conductor 88 after discontinuing the voltage, it is believed that the potential difference across the conductors 88 and 90 is removed. Thus, the amount of ion loss (i.e., corrosion) is minimized because the potential difference between the conductors has been reduced or eliminated and little to no electrochemical reaction occurs.

As discussed above, electrochemical reactions are generally driven by having current at a first conductor and a drain or ground at the second conductor thereby creating the potential difference between the conductors. As the first conductor remains at a higher voltage than the second conductor, it drives the metal ions from the first conductor to the second conductor and increases the corrosion on the first conductor. In some embodiments, the processor and the circuit may be used to reverse the polarity of the conductors on a periodic basis to minimize the extent of the corrosion on one conductor to the point of failure.

Figure 10:
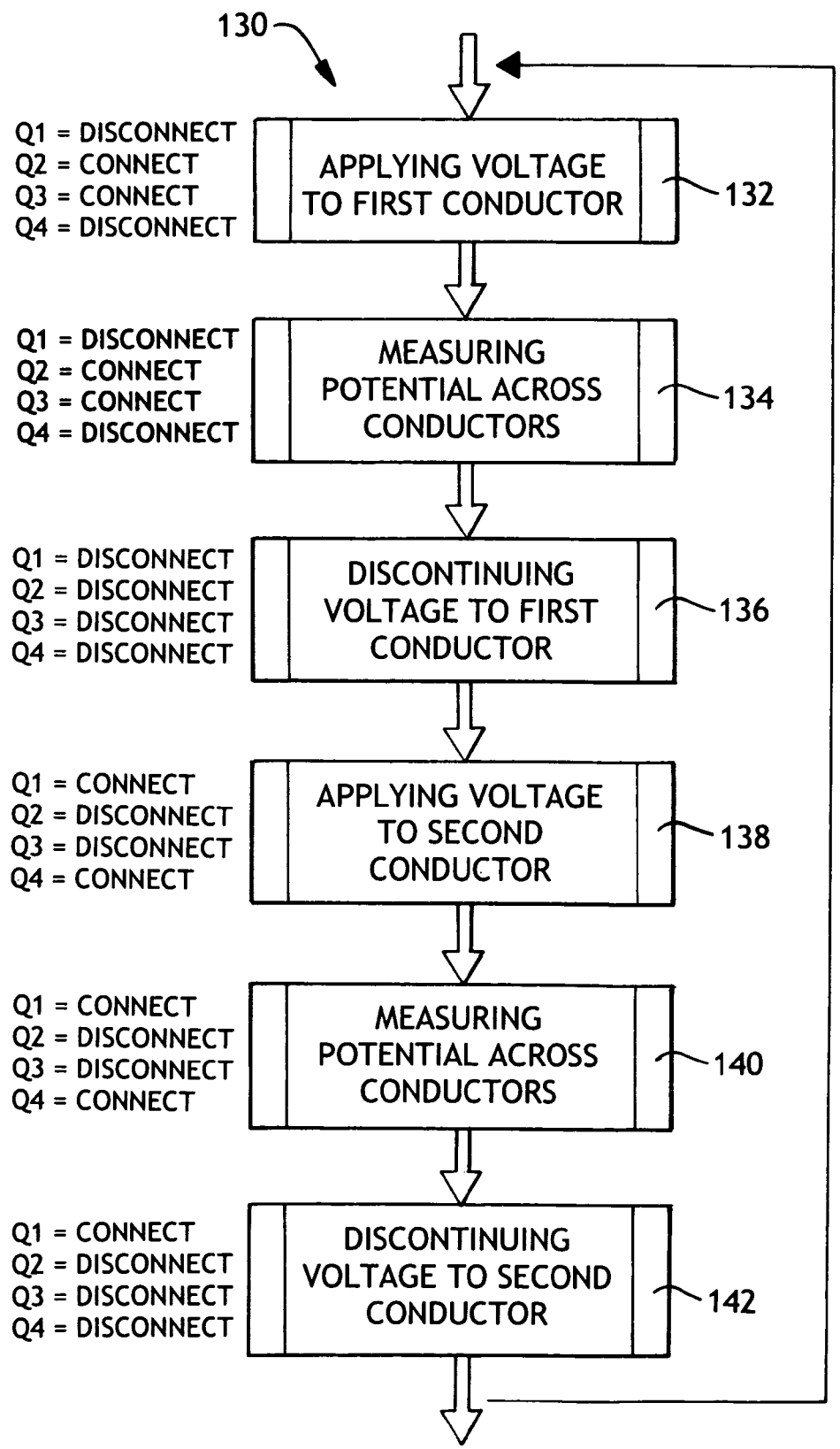
FIG. 10 is a flow diagram illustrating a sequence of programming steps of one embodiment.

For example, referring now to FIG. 10, a third sequence of steps is illustrated generally at 130. The third sequence of steps 130 includes a first step 132 of applying voltage to the first conductor 88; a second step 134 of measuring the potential across the conductors 88 and 90; a third step 136 of discontinuing the voltage to the first conductor 88. Steps one 132, two 134, and three 136 are similar to the steps 108, 110, and 112 of the first sequence 106. Specifically, in various embodiments, steps 132 and 134 may be accomplished by connecting transistors Q2 and Q3 and disconnecting transistors Q1 and Q4. In various embodiments, step 136 may be accomplished by disconnecting transistors Q1, Q2, Q3, and Q4.

The third sequence of steps 130 includes additional steps 138, 140, and 142. Step 138 includes applying voltage to the second conductor 90 after discontinuing the voltage to the first conductor 88. The additional step of applying voltage to the second conductor 90 may be accomplished by controlling a circuit 102 as illustrated in FIG. 7. Specifically, step 138 of the third sequence 130 may be accomplished by connecting transistor Q1 and Q4 and disconnecting transistors Q2 and Q3. As such, the first conductor 88 is disconnected from the voltage source 114 and second conductor 90 is connected to the voltage source 114. In this configuration, the current is in a second direction 94 from the voltage source 114 to the second conductor 90 through the sensor 72 (i.e., the space between the conductors) to the first conductor 88 and then to the ground 116. By reversing the direction of flow, it is believed that at least some of the ions that are moving away from a first sensor 88 towards a second sensor 90 may be reversed and the amount of ion loss (i.e., corrosion) may be minimized.

Step 140 includes measuring the potential across the conductors 88 and 90 while still applying voltage to the second conductor 90. This step may be accomplished by controlling a circuit 102 as illustrated in FIG. 7. Specifically, step 140 of the third sequence 130 may be accomplished by connecting transistors Q1 and Q4 and disconnecting transistors Q2 and Q3. As such, first conductor 88 is disconnected from the voltage source 114 and second conductor 90 is connected to the voltage source 114. Likewise, first conductor 88 is connected to the ground 116 whereas second conductor 90 is disconnected from the ground 116.

Finally, the third sequence 130 includes the step 142 of discontinuing voltage to the second conductor 90. The step 142 of discontinuing voltage to the second conductor 90 may be accomplished by controlling a circuit 102 as illustrated in FIG. 7. Specifically, step 142 of the third sequence 130 may be accomplished by disconnecting transistor Q1, Q2, Q3, and Q4. As such, second conductor 90 is disconnected from the voltage source 114.

In various embodiments, voltage may be applied to the first or second conductors for any suitable percentage of time. For example, in various embodiments, the voltage may be applied to the first conductor 88 and/or the second conductor 90 for 10% or less, 5% or less, or 1% or less of the time. In other words, the first conductor 88 and/or the second conductor 90 may have voltage applied 10% or less of the time and may have no voltage applied 90% or more of the time. Likewise, the first conductor 88 and/or the second conductor 90 may have voltage applied 5% or less of the time and may have no voltage applied 95% or more of the time. In some embodiments, the first conductor 88 and/or the second conductor 90 may have voltage applied 2% or less of the time and may have no voltage applied 98% or more of the time.

Figure 11:
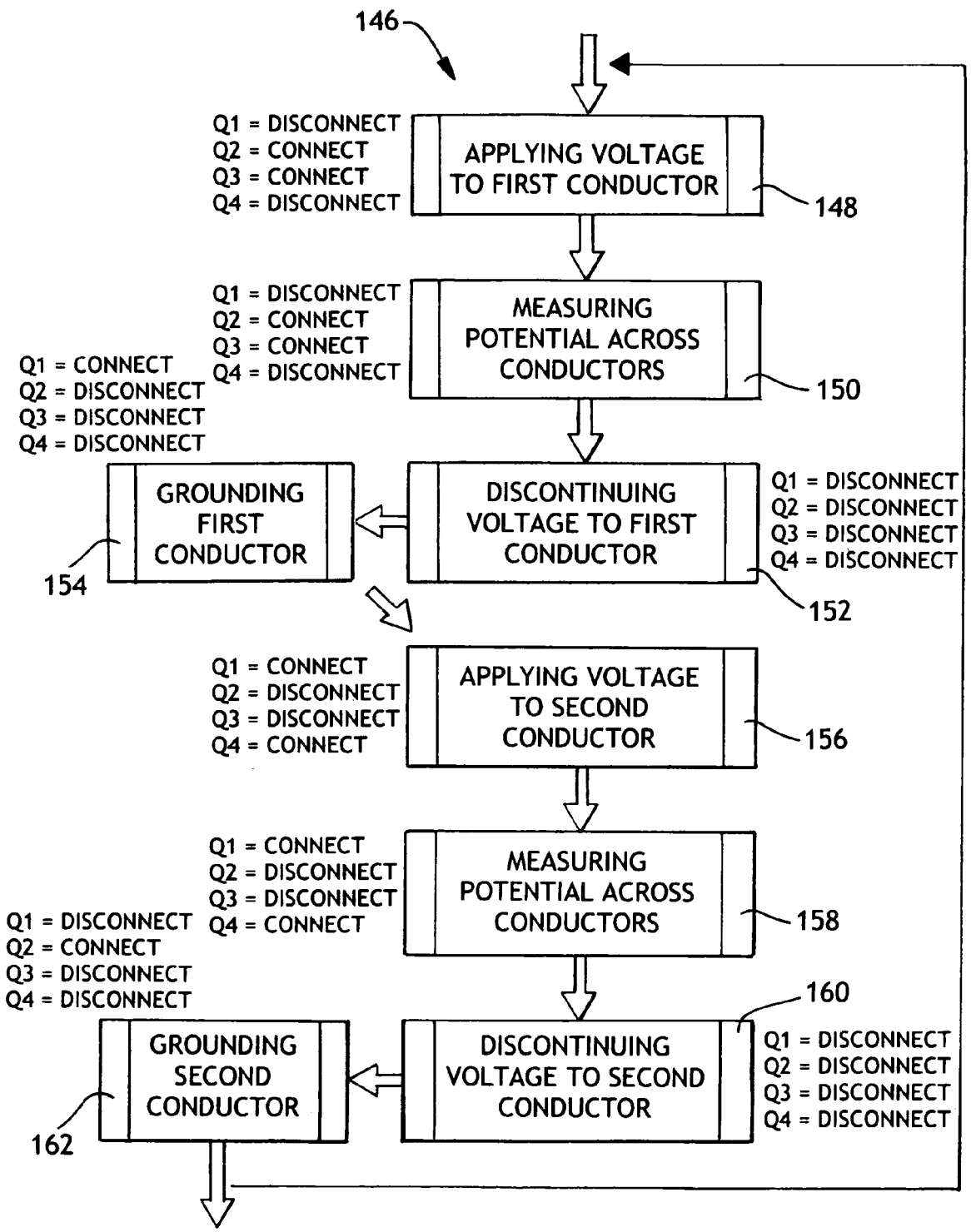
FIG. 11 is a flow diagram illustrating a sequence of programming steps of one embodiment.

In some embodiments, a sequence of steps may include the steps of alternating the direction of current flow and grounding the conductors after discontinuing the current. For example, referring now to FIG. 11, a fourth sequence of steps is illustrated generally at 146. The fourth sequence of steps 146 includes a first step 148 of applying voltage to the first conductor 88; a second step 150 of measuring the potential across the conductors 88 and 90; a third step 152 of discontinuing the voltage to the first conductor 88; and a fourth step 154 of grounding the first conductor 88. Steps one 148, two 150, three 152, and four 154 may be accomplished in a similar manner as that described for steps 120, 122, and 124, and 126 respectively of the second sequence 118. Specifically, steps 148 and 150 may be accomplished by connecting transistors Q2 and Q3 and disconnecting transistors Q1 and Q4. Step 152 may be accomplished by disconnecting transistors Q1, Q2, Q3, and Q4. Step 154 may be accomplished by, for example, connecting transistor Q1 and disconnecting transistors Q2, Q3, and Q4.

The fourth sequence of steps 146 includes a fifth step 156 of applying voltage to the second conductor 90; a sixth step 158 of measuring the potential across the conductors 88 and 90; and a seventh step 160 of discontinuing the voltage to the second conductor 90. Steps five 156, six 158, and seven 160 may be accomplished in a similar manner as that described for steps 138, 140, and 142 of the third sequence 130. Specifically, steps 156 and 158 may be accomplished by connecting transistors Q1 and Q4 and disconnecting transistors Q2 and Q3. Step 160 may be accomplished by disconnecting transistors Q1, Q2, Q3, and Q4.

Finally, the fourth sequence of steps 146 includes the step 162 of grounding the second conductor 90 after discontinuing the voltage to the second conductor 90 in step seven 160. Step 162 may be accomplished by connecting transistor Q2 and disconnecting transistors Q1, Q3, and Q4.

This embodiment is believed to reduce conductor corrosion by implementing three different strategies: pulsing the current on and off, reversing the flow of current, and grounding the conductors after disconnecting the current. Since the microcontroller is not directing the sampling of the conductor continuously, the conductor excitation voltage need only be applied slightly before the sampling step. Likewise, as soon as the sample has been completed, the excitation voltage may be removed and thus, the duty cycle of excitation voltage will be less than if continuously excited. Therefore, the life of the conductors is expected to be extended. In other words, the current flow is cycling between a flowing condition and a stopped condition (i.e., the current is pulsed).

Additionally, this combination also reverses the current between a first direction 92 and a second direction 94. By reversing the direction of flow, it is believed that at least some ions that are moving away from a first sensor 88 towards a second sensor 90 may be reversed and at least some ions that are moving away from a second sensor 90 towards a first sensor 88 may be reversed. Thus, the overall amount of ion loss (i.e., corrosion) may be minimized by reducing the mobility of the ions in solution.

Finally, by grounding the first conductor 88 and/or the second conductor 90 after discontinuing the voltage, it is believed that the potential difference across the conductors 88 and 90 is removed. Thus, the amount of ion loss (i.e., corrosion) is minimized because the potential difference between the conductors has been reduced or eliminated and little to no electrochemical reaction occurs.

In various embodiments, the methods of reducing corrosion may have any suitable cycle rate. In other words, the sequence of steps may be repetitively executed any suitable number of times in any suitable time frame. For example, the sequence of steps 106, 118, 130, and/or 146 may be repetitively executed at least one time per second, at least two times per second, at least three times per second, or at least four times per second. In some embodiments, the programming instructions may include a variable cycle rate. For example, the sequence of steps 106, 118, 130, and/or 146 may be repetitively executed at a first frequency for a first time period and may be repetitively executed at a second frequency for a second time period wherein the first frequency and the second frequency are different. For example, the microprocessor may include programming instructions that repetitively execute the sequence of steps 106, 118, 130, and/or 146 at a first frequency while no insult is detected and may repetitively execute the sequence of steps at a second frequency when an insult is detected. In some embodiments, the second frequency may be higher or may be lower. For example, in one embodiment, the sequence of steps 106, 118, 130, and/or 146 is executed 3 times per second when the absorbent article is dry and 100 times per second when the absorbent article has been insulted.

In various embodiments, the methods of reducing corrosion may include applying voltage to the first conductor 88 or the second conductor 90 for any suitable percentage of time. For example, in various embodiments, the voltage may be applied to the first conductor 88 and/or the second conductor 90 for 10% or less, 5% or less, or 1% or less of the time. In other words, the first conductor 88 and/or the second conductor 90 may have voltage applied 10% or less of the time and may have no voltage applied 90% or more of the time. Likewise, the first conductor 88 and/or the second conductor 90 may have voltage applied 5% or less of the time and may have no voltage applied 95% or more of the time. In yet other embodiments, the first conductor 88 and/or the second conductor 90 may have voltage applied 2% or less of the time and may have no voltage applied 98% or more of the time. It is believed that by applying voltage for small percentages of time the duty cycle of excitation voltage is low. Since the conductors are energized for less time than they are not energized, the life of the conductors is expected to be significantly extended.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto.

What is claimed is:

1. A method of reducing sensor corrosion in an absorbent article comprising,
    providing a monitor adapted to electrically connect with a wetness sensor integrated with an absorbent article, the wetness sensor having a first conductor and a second conductor, the monitor comprising programming instructions that, when attached to the sensor in the absorbent article and activated, execute a sequence of steps, wherein the sequence of steps includes,
    applying voltage to the first conductor of the wetness sensor,
    measuring the potential across the conductors,
    discontinuing the voltage to the first conductor, and
wherein the sequence of steps is repetitively executed at least one time per second and the voltage is applied to the first conductor for 10% or less of the time and the voltage is discontinued to the first conductor 90% or more of the time.

2. The method of claim 1 wherein the instructions further comprise repetitively executing the sequence of steps at least three times per second.

3. The method of claim 2 wherein the voltage is applied to the first conductor for 5% or less of the time and the voltage is discontinued to the first conductor 95% or more of the time.

4. The method of claim 1 wherein the instructions further comprise repetitively executing the sequence of steps at a first frequency for a first time period and repetitively executing the sequence of steps at a second frequency for a second time period wherein the first frequency and the second frequency are different.

5. The method of claim 1 wherein the instructions further comprise the step of grounding the first conductor after discontinuing the voltage to the first conductor.

6. The method of claim 1 wherein the instructions further comprise the steps of
    applying voltage to the second conductor after discontinuing the voltage to the first conductor,
    measuring the potential across the conductors, and
    discontinuing the voltage to the second conductor.

7. The method of claim 6 wherein the instructions further comprise the steps of,
    grounding the first conductor after discontinuing the voltage to the first conductor and
    grounding the second conductor after discontinuing the voltage to the second conductor.

8. A method of reducing sensor corrosion in an absorbent article comprising,
    providing a monitor adapted to electrically connect with a wetness sensor integrated with an absorbent article, the wetness sensor having a first conductor and a second conductor, the monitor comprising programming instructions that, when attached to the sensor in the absorbent article and activated, repetitively execute a sequence of steps including,
    applying voltage to the first conductor,
    measuring the potential across the conductors,
    discontinuing the voltage to the first conductor,
    applying voltage to the second conductor,
    measuring the potential across the conductors, and
    discontinuing the voltage to the second conductor.

9. The method of claim 8 wherein the instructions further comprise repetitively executing the sequence of steps at least one time per second.

10. The method of claim 8 wherein the instructions further comprise repetitively executing the sequence of steps at least three times per second.

11. The method of claim 8 wherein the instructions further comprise repetitively executing the sequence of steps at a first frequency for a first time period and repetitively executing the sequence of steps at a second frequency for a second time period wherein the first frequency and the second frequency are different.

12. The method of claim 8 wherein the voltage is applied to the first conductor for 10% or less of the time and the voltage is discontinued to the first conductor 90% or more of the time.

13. The method of claim 12 wherein the voltage is applied to the second conductor for 10% or less of the time and the voltage is discontinued to the second conductor 90% or more of the time.

14. The method of claim 8 wherein the instructions further comprise the step of grounding the first conductor after discontinuing the voltage to the first conductor.

15. The method of claim 8 wherein the instructions further comprise the steps of,
    grounding the first conductor after discontinuing the voltage to the first conductor and
    grounding the second conductor after discontinuing the voltage to the second conductor.

16. A method of reducing sensor corrosion in an absorbent article comprising,
    providing a monitor adapted to electrically connect with a wetness sensor included in an absorbent article, the wetness sensor having a first conductor and a second conductor, the monitor comprising programming instructions that, when attached to the absorbent article and activated, repetitively execute a sequence of steps including,
    applying voltage to the first conductor,
    measuring the potential across the conductors,
    discontinuing the voltage to the first conductor,
    grounding the first conductor,
    applying voltage to the second conductor,
    measuring the potential across the conductors,
    discontinuing the voltage to the second conductor, and
    grounding the second conductor.

17. The method of claim 16 wherein the instructions further comprise repetitively executing the sequence of steps at least one time per second.

18. The method of claim 16 wherein the instructions further comprise repetitively executing the sequence of steps at least three times per second.

19. The method of claim 16 wherein the instructions further comprise repetitively executing the sequence of steps at a first frequency for a first time period and repetitively executing the sequence of steps at a second frequency for a second time period wherein the first frequency and the second frequency are different.

20. The method of claim 16 wherein the voltage is applied to the first conductor for 10% or less of the time and the voltage is discontinued to the first conductor 90% or more of the time and the voltage is applied to the second conductor for 10% or less of the time and the voltage is discontinued to the second conductor 90% or more of the time.

* * * * *